United States Patent [19]

Caprari et al.

[11] 4,432,641
[45] Feb. 21, 1984

[54] VISUAL DEFECT INSPECTION OF MASKS

[75] Inventors: Fausto Caprari, East Brunswick; Robert A. Geshner, Lebanon, both of N.J.

[73] Assignee: RCA Corporation, New York, N.Y.

[21] Appl. No.: 312,277

[22] Filed: Oct. 16, 1981

[51] Int. Cl.³ .................... G01N 21/88; G02B 21/08
[52] U.S. Cl. .................................... 356/237; 350/523
[58] Field of Search ............... 350/235, 236, 237, 523; 356/237, 429, 430; 353/38 (U.S. only), 102; 362/268

[56] References Cited

U.S. PATENT DOCUMENTS 3,318,184 5/1967 Jackson ........................... 353/102 X
3,860,335 1/1978 Caprari ............................... 353/102

OTHER PUBLICATIONS

R. Kingslake, *Applied Optics and Optical Engineering*, vol. 1, pp. 10–16, 1965, New York and London.
L. C. Martin, *An Introduction to Applied Optics*, vol. II, pp. 218–222, 1932, London.
Hardy and Perrin, *The Principles of Optics*, pp. 536–537, 1932, published by McGraw Hill.

*Primary Examiner*—Vincent P. McGraw
*Assistant Examiner*—L. A. Dietert
*Attorney, Agent, or Firm*—Birgit E. Morris; Donald S. Cohen; Joseph D. Lazar

[57] ABSTRACT

An optical system and method for direct human eye visual inspection of specimens of photoresist coated masks for defects as small as 2 μm. The specimens are uniformly illuminated with a partially coherent sodium light that has very high illuminance and constrast levels. The system consists of a high pressure (1–1.5 atmosphere) sodium lamp source projected onto the specimen by a Kohler-type illumination system.

5 Claims, 1 Drawing Figure

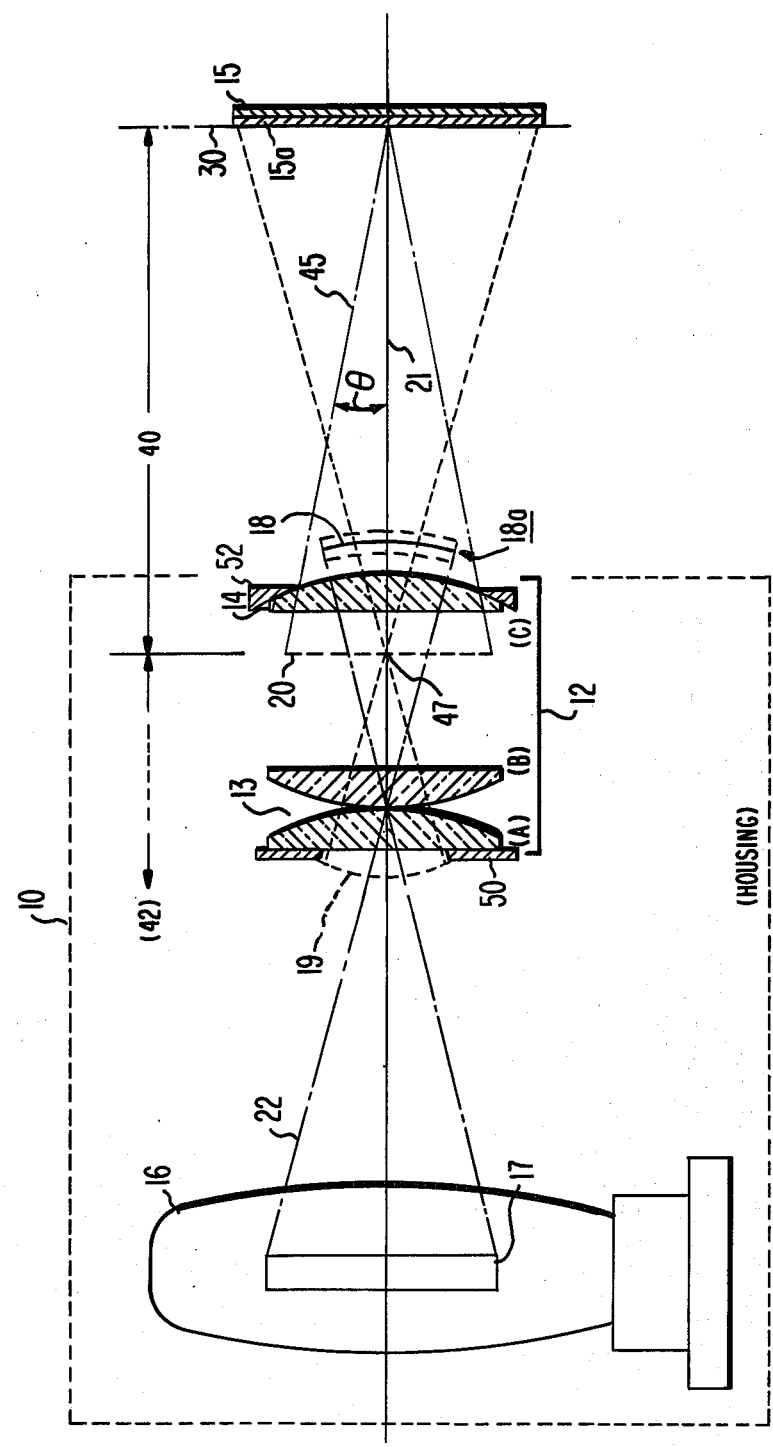

VISUAL DEFECT INSPECTION OF MASKS

This invention relates to a method and system for visually inspecting masks and, more particularly, masks that have been coated with photoresist material.

BACKGROUND OF THE INVENTION

Photoresist coated mask blanks are visually inspected with or without microscopes in the prior art filtered tungsten halogen lamps. For direct visual relection systems the lamp is placed at the focal point of a parabolic reflector. Blue light is absorbed by the filter to avoid exposure of the photoresist layer and infrared radiation is absorbed to minimize harmful heating effects, which expands the mask and causes misregistration thereby. The difficulty in using such a prior art reflectors are that (1) large reflectors and filters in the order of 6" (15 cm) in diameter are required to illuminate 100% of the surface of the mask; (2) only a very small percentage, namely in the order of about 10%, of the radiant energy emitted by the tungsten halogen lamp can be used for inspection purposes, resulting thereby in inadequate intensity of illumination and consequent low light scattering levels of visual defects; and (3) there is relatively short life in the order of 200 hours for the tungsten halogen lamp, resulting thereby in high maintenance costs.

For microscopic inspection systems, also using tungsten halogen lamps, defects as small as ½ micrometer can be detected. But such an inspection takes 30 minutes.

There is a need in the art for an improved technique for the visual inspection of masks of the type that are coated with a photoresist material.

SUMMARY OF THE INVENTION

According to the present invention, an optical system for visual inspection of specimens of photoresist coated masks comprises a light source derived from a predetermined length of an elongated arc of sodium oriented perpendicularly to an optical axis. A Kohler-type illumination system, is used to focus the light source within the exit pupil of the system. A specimens positioned at the image plane is uniformly illuminated at significantly high scatter levels and high illuminance levels so that defects to at least 2 μm in diameter on a specimen at the image plane are easily detected by direct human eye inspection.

BRIEF DESCRIPTION OF THE DRAWING

The sole FIGURE of the drawing is a schematic of a preferred embodiment of the inspection system of the invention.

DETAILED DESCRIPTION OF THE PREFERRED EMBODIMENT

As shown in the drawing, a projection lens housing 10 provides light for illuminating a mask 15 having a photoresist coating 15a. The housing 10 contains a sodium light lamp 16 which provides an elongated sodium arc 17. Arc 17 provides a beam of light 22 in the illuminating light spectrum comprising sodium. The beam 22 is passed through a lens system 12 formed of an input pair (A and B) of plano-convex lens elements 13 and thence to a single (C) output plano-convex lens element 14 to develop an effective light source image 18 within exit pupil of the lens system 12 represented by the curved portion 18a. Lens A is provided with a rim 50 to stop the lens to 2.5 inches (6.35 cm). Lens C is stopped by rim 52 to 3.25 inches (8.25 cm.) to be described in detail hereinafter. Image 18 is the conjugate of the arc 17 and is of reduced size, at about 0.66 inches (1.7 cm), the arc 17 being about 2 inches (5.1 cm).

The mask 15 is positioned so that the photoresist coating 15a is at the image plane 30 of the system. With the optics comprising lens elements 13 and 14, as will be further described, the illumination image at the coating 15a of the mask 15 derives from the aerial illumination surface 19 adjacent the lens element A of the lens element 13.

Lamp 16 is preferably a Lucalox lamp manufactured by the General Electric Company. It is the type that is operated with a sealed pressure of about 1 to 1½ atmospheres within the casing of the lamp 16 and is thus termed a "high" pressure lamp. Suitable starting components such as an amalgam of sodium, mercury and xenon is provided in the lamp and energized by a coiled tungsten coated electrode not shown. For the present embodiment the Lucalox lamp used rated at 100 watts and provides 95 lumens/watt. In order to provide the high level of illumination (>1000 foot candles) required to practice the invention, a sodium lamp of this type provides the best illumination known to us that is available in the art. Nevertheless the difficulty with such a lamp is that it undesirably provides an elongated arc 17 having an approximate dimension of about 2" in length and a ¼" in diameter (51 mm long by 6 mm wide).

According to this invention, a substantially uniform field of illumination is provided at the surface of the photoresist coating 15a even with a non-symmetrical light source. The uniform field is necessary in order to provide the high level of uniform illumination needed to scatter the light from defects on the surface of the coating 15a. The sort of defects that are of importance to identify in this art are pinholes of sizes as little as 2 μm. Heretofore such small defects have been found to be very difficult to identify except by the use of a microscope. They surely have not been able to be identified by the naked human eye. Microscopic techniques are the typical methods used to identify defects in the form of pinholes to this small dimension. We have now discovered that by properly illuminating the coating with light, pinholes will function as a scattering mechanism manifesting diffraction effects. Pinholes are known to scatter light such that a 2 μm pinhole will develop an apparent light source in the order of 200 μm, which 200 μm sizes are visually discernible to the naked eye provided the light is uniform with sufficient contrast effects at the surface of the photoresist coating.

In order to achieve a high degree of uniform illumination at the image plane 30, the aerial surface 19, which is the conjugate surface of plane 30, must also be uniformly illuminated. This is achieved by applying the principle of the law of inverse-squares to convert the elongated sodium arc 17, which is obviously asymmetrical, into a symmetrical field such as an extensive circular pattern required for effectively illuminating mask 15. See *Applied Optics and Optical Engineering*, edited by R. Kingslake, Vol. 1, pp. 10–16, for a description of the inverse-square law. According to the conventional use of the inverse-square law, the distance between the assymetrical light source 17 to the aerial surface 19 is arranged typically to be on the order of approximately 10 times the length of the asymmetrical light source to achieve a symmetrical illumination pattern. In the present example, the sodium arc 17 is 2" (5 cm) long. Applying the inverse-square law to the present example in the conventional sense just described would require a distance of 20" (50 cm) between arc 17 and surface 19. In the design of one embodiment of the invention we have discovered that this distance was not necessary and found that a distance of 4 inches (10 cm) between the arc 17 and aerial surface 19 provided sufficient illumination to scatter the pinholes across a defective square (5"×5") mask sufficiently for visual observation as will be further explained.

The lens elements A and B of the lens 13 serving as a condenser lens and of the single lens C of the lens 14 are designed according to conventional optical design practices. One of the critical parameters in the design is the numerical aperture (NA) required to provide the desired illumination. It is well known that the larger the numerical aperture, the higher the illumination level. It is also known that the numerical aperture is related to the cone angle of the lens 14. In particular, it is known that the half-angle $\theta$ of the bundle of rays 45 is equal to the $\sin^{-1}$ of the numerical aperture. In the present design, this value is 0.162 for an angle $\theta$ of 9.3°.

In addition, the magnification of the lens system 12 was designed to be about four. For such a magnification, a circle on aerial surface 19 will be magnified at the image plane 30 to be equivalent to a 9.5 inches (24 cm.) diameter of a circular illuminated pattern. It is known that the effective square that can be developed from a circle is about 0.7 of the diameter of the circle. Accordingly, for the present embodiment, the 9.5" illuminated pattern at image plane 30 would be adequate to take a 6×6 inch square mask which capability is far ahead of the present (5×5 inch square) state of the art requirements for masks.

In the practice of the invention, a high degree of uniform illumination is achieved by precisely positioning the lens elements A, B and C in relation to the image plane 30 and aerial surface 19. Lenses A, B and C are designed in accordance with conventional geometric optic lens design as mentioned above. The diameter of surface 19 is defined by the rim 50 of lens A. The size of rim 50 of lens A multiplied by the magnification of lens system 12 determine the circular size of the mask 15 that can be illuminated from the arc 17. Accordingly, in the design of these lenses, the diameters and focal lengths are selected in accordance with the size of the mask and the desired N.A. In the preferred embodiment $\theta$ is 9.3° whereby the numerical aperture is 0.162. With the sizes of the lenses determined by conventional calculation, based on the combined focal length (FL) of lens 12, and numerical aperture (N.A.), the precise positioning of the lens elements in relation to the conjugate surfaces 30 and 19 is determined by known ray plotting methods. See Jenkins and White on *Fundamentals of Optics,* McGraw Hill, 1957, pp. 52–53, for a description of such a method. Experimental bench tests have been used to verify that the ray plotting method is excellent to design a system according to this invention.

The invention utilizes a Kohler-type illumination system that is arranged to achieve a relatively high intensity of illumination at the image plane 30 and yet achieve substantial uniformity of illumination at the image plane 30 at which the specimen, namely the coating 15a of the mask 15, is positioned. In a conventional Kohler illumination system as used, for example, for projection systems utilizing slides, the image of the light source is focused at the nodal point 47 in the entrance pupil 20 of the system rather than at the aerial image 18.

Moreover, the slide is typically positioned to the right of lens B and is as close to the surface of lens B as possible. According to the present invention, the aerial surface 19 is positioned to the left of lens element A and the image of the sodium arc 17 is located near the exit pupil of lens element C within portion 18a as indicated by the dotted lines. It should be noted and understood that the present invention provides illumination of the coating 15a. As such, the present invention is not an image system, whereby, no slide is needed or used.

In conventional geometric optics, the space 40 between the nodal point 47 within the entrance pupil 20 and the image plane 30 is called the image space 40, while the space to the left of the nodal plane of entrance pupil 20 is termed the object space 42. According to that convention the light source image 18 of the lens system 12 of this invention is located in the image space 40 and the aerial surface 19 is located in the object space 42. Moreover, in conventional geometric optics using a conventional Kohler illumination system, maximum achievable uniformity exists at the image plane corresponding image plane 30 herein. See a discussion and analysis of such systems by L. C. Martin, in his *An Introduction to Applied Optics,* Vol. II, pp. 218–222, published in London 1932 by Sir Isaac Pitman & Sons, Ltd. According to one possible arrangement of the present illumination system with the image 18 produced at the exit of lens C, the maximum intensity of the image plane 30 exists when the lamp image 18 is positioned as close as possible to the plane 30. However, with such maximum image intensity, the elongated sodium arc 17 will be essentially focused as an elongated arc at the image plane 30, thereby establishing a quite nonuniform distribution of illumination at the image plane 30 and thus over the entire surface of the coating 15a. By properly positioning the image 18 of the sodium arc 17 in the image space 40 so that a substantially circular pattern of illumination is achieved at image plane 30, there is a reduction from a maximum of the illumination intensity but there is achieved a more uniform distribution of the light at both conjugate surfaces 30 and 19 of the lens system 12. In such a position the diameter of the image 18 is smaller than both the length of the sodium arc 17 and the diameter of the entrance pupil 20. By the proper arrangement of the three lenses A, B and C of the Kohler-type illumination system 12 according to the invention, the illumination at the aerial surface 19 can be substantially uniform with reduced intensity by the rim 50.

It is important to understand that in a slide projector system of the type using the classic Kohler illumination system, both uniformity and intensity of the light illumination are measured without the slide in position. Moreover, such a Kohler system does not define the location of the object surface with respect to the so-called condenser lens. See Vol. 2, pp 225–226, of the above-mentioned Kingslake text; also, see *The Principles of Optics,* pp 536–537 by Hardy and Perrin, McGraw Hill, 1932, as well as the above-mentioned Martin text, for a description of a slide projector using Kohler illumination. See also, U.S. Pat. No. 3,860,335 for an optical mask projection system using 3 lens elements.

We have discovered that a substantial uniformity of illumination (±10%) with excellent although not maximum intensity is achieved at the aerial surface 19 and thus at the conjugate thereof, namely image plane 30, by experimentally positioning the lenses A, B and C relative to the sodium arc source 17 for the above-described balance of intensity and uniformity. Moreover, the distance between the aerial surface 19 and the arc 17 is not ten times the length of the arc 17 as typically followed under the inverse square law but is only two times that length.

By the arrangement described, the very high although not maximum level of illuminance is achieved with a high numerical aperture defined by the angle $\theta$ and the relatively high coherency factor. As known, the coherency factor is determined by the diameter of the effective source 18 to the diameter of the entrance pupil 20.

In operation, the high intensity illumination field on the surface of the coating 15a is focused by the projection lens 12. The arc 17 is focused by the double lens elements A and B and single lens C into the effective light source image 18 in the image space between planes 20 and 30 within the exit pupil of lens element C. Partial coherence ($\sigma=0.2$) is achieved in this optical system, since the effective light source image 18 is a reduced image of the arc 17 and is thereby underfilling the entrance pupil 20 to the lens system 12. There is a high contrast level achieved at the image plane 30 in conjunction with a very high level of illuminance because of partial coherence and high numerical aperture.

The spectral energy distribution of the high pressure sodium lamp 16 is in the yellow-orange region and does not expose or heat up the photoresist layer 15a of the mask 15. Moreover, the 100 watt high pressure sodium lamp 16 has a very high luminous efficiency of about 95 lumens/watt and moreover has a long life of about 12,000 hours.

As indicated above, a 9½" (24 cm) diameter field of illumination can indeed be obtained at 10" (25 cm) distance from the single lens element 14 with a uniformity of about ±10%.

A preferred design of a system of the invention provided the means to visually inspect with the naked eye photoresist coated masks for defects. The following table lists the critical parameters of that system:

TABLE I

| | |
|---|---|
| System Magnification | 3.77× |
| Sodium Arc Reduction | 3× |
| Focal Length of Lens System 12 | 2.7" |
| N.A. of Lens System 12 | 0.162 |
| Illuminance at Mask Surface | 1500 Foot Candles |
| Size of Lens Elements A and B | 3.5" Diam. (each) |
| Rim Size (50) of Lens A | 2.5" I. Diam. |
| Size of Lens Element C | 3.5" Diam. |
| Rim Size of Lens C | 3.25" (I. Diam.) |
| Spacing Between Lens Double A/B and Lens C | 3" |
| Size of Illumination Field (Image) | 9.5" (24.1 cm) Diameter |
| Coherency Factor ($\sigma$) | 0.2 |

What we claim is:

1. A method for visually inspecting specimens of photoresist coated masks having a sensitivity to radiation in the blue and ultra-violet wave length spectrum, comprising:
   (a) generating an elongated light source of sodium light said source of light being substantially free of radiation in the blue and ultra-violet wave length spectrum;
   (b) focusing said source in a Kohler-type illumination system within the exit pupil thereof;
   (b1) said Kohler-type illumination system having at least three lens elements, comprising two contiguous input lens elements and spaced therefrom one output lens element, wherein an aerial surface of uniform illuminance is located between said three lens elements and the source, an entrance pupil plane is located at the input side of the output lens element, and an image surface plane is located at the output side of said output lens element;
   (c) imaging said light source as an aerial image within the exit pupil of said lens system at an aerial surface that is a conjugate of said light source; and
   (d) projecting a substantially uniform illuminance field on a specimen positioned at a plane that is conjugate to said aerial surface of uniform illuminance with sufficiently high contrast levels and illuminance levels to detect with the human eye defects as small as 2 µm by scattering light from said defects.

2. An optical system for visual inspections of specimens of photoresist coated masks having a sensitivity to radiation in the blue and ultra-violet wave length spectrum comprising:
   (a) a light source consisting of a predetermined length of an elongated sodium arc oriented perpendicularly to the optical axis of the system said source of light being substantially free of radiation in the blue and ultra-violet wavelength spectrum;
   (b) a Kohler-type illuminating system for projecting a uniform field of illuminance onto a specimen plane located in the image plane of said system;
   (bi) said Kohler-type system comprising a pair of plano-convex positive lens elements positioned along said optical axis proximate to an aerial surface of uniform illuminance, and a single plano-convex lens element positioned on said optical axis remote from said aerial illuminance surface;
   (bii) the aerial illuminance surface of said system being located between said pair of lens elements and said source, and the plane of the entrance pupil of said lens system lying between said pair of said adjacent lenses and single lens elements;
   (biii) said system being positioned between said source and specimen plane and arranged to provide a conjugate image of said light source between said single lens element and said specimen plane that is smaller in diameter than both said sodium arc length and said entrance pupil diameter;
   whereby a specimen positioned at said specimen plane is uniformly illuminated at significantly high contrast levels and high illuminance levels so that defects to at least 2 µm in diameter on said specimen are easily detected by direct human eye inspection.

3. A system according to claim 2, wherein said sodium lamp source is a 100 watt lamp that provides 95 lumens per watt, having an elongated arc of approximately 2" (5 cm) long.

4. A system according to claim 3, wherein said specimen is about 9½" (24 cm) in diameter and is spaced 10" (25 cm) from said single lens.

5. A method according to claim 1, wherein said beam of light source is partially coherent by providing a reduced image of the source that is smaller than the entrance pupil of the illumination system.

* * * * *